United States Patent [19]
Benning et al.

[11] Patent Number: 5,540,077
[45] Date of Patent: Jul. 30, 1996

[54] METHOD AND GAS MIXTURE FOR CALIBRATING AN ANALYZER

[75] Inventors: Michael A. Benning, Allentown; Stephen B. Miller; James S. Wallis, both of Doylestown; Richard B. Kowey, Souderton, all of Pa.

[73] Assignee: Scott Specialty Gases, Inc., Plumsteadville, Pa.

[21] Appl. No.: 258,432

[22] Filed: Jun. 10, 1994

[51] Int. Cl.$^6$ .................................................. G01D 18/00
[52] U.S. Cl. .................................................. 73/1 G
[58] Field of Search .................................................. 73/1 G

[56] References Cited

U.S. PATENT DOCUMENTS

| | | | |
|---|---|---|---|
| Re. 29,383 | 9/1977 | Gallatin et al. | 73/861.44 X |
| 3,657,920 | 4/1972 | Teel et al. | 73/28.04 |
| 3,853,321 | 12/1974 | Dahneke | 73/865.5 X |
| 3,922,905 | 12/1975 | Roth | 73/28.04 |
| 4,114,419 | 9/1978 | Kimbell | 73/1 G |
| 4,121,455 | 10/1978 | Haslett et al. | 73/861.04 |
| 4,485,665 | 12/1984 | Norman | 73/29.01 |
| 4,753,095 | 6/1988 | Jones, Jr. et al. | 73/3 X |
| 4,974,455 | 12/1990 | McGowan et al. | 73/863.12 |
| 5,296,113 | 3/1994 | Seger et al. | 204/153.18 |
| 5,307,668 | 5/1994 | Vander Heyden | 73/30.02 |

*Primary Examiner*—Thomas P. Noland
*Attorney, Agent, or Firm*—Dykema Gossett PLLC

[57] ABSTRACT

A method of measuring the concentration of a component in a sample gas comprises the steps of: determining the flow rate at sonic velocity of a sample gas through a critical orifice; determining the flow rate at sonic velocity of a calibration gas through the critical orifice; comparing the flow rate of the sample gas with the flow rate of the calibration gas; formulating the calibration gas with an additional gas to adjust the flow rate of the calibration gas to approximately equal the flow rate of the sample gas through the critical orifice at sonic velocity, thereby creating a balanced calibration gas; calibrating the analyzer with the balanced calibration gas, wherein a concentration reading of the component from the analyzer is compared with a known concentration of the component in the balanced calibration gas; and measuring the concentration of the component of the sample gas using the analyzer.

19 Claims, 1 Drawing Sheet

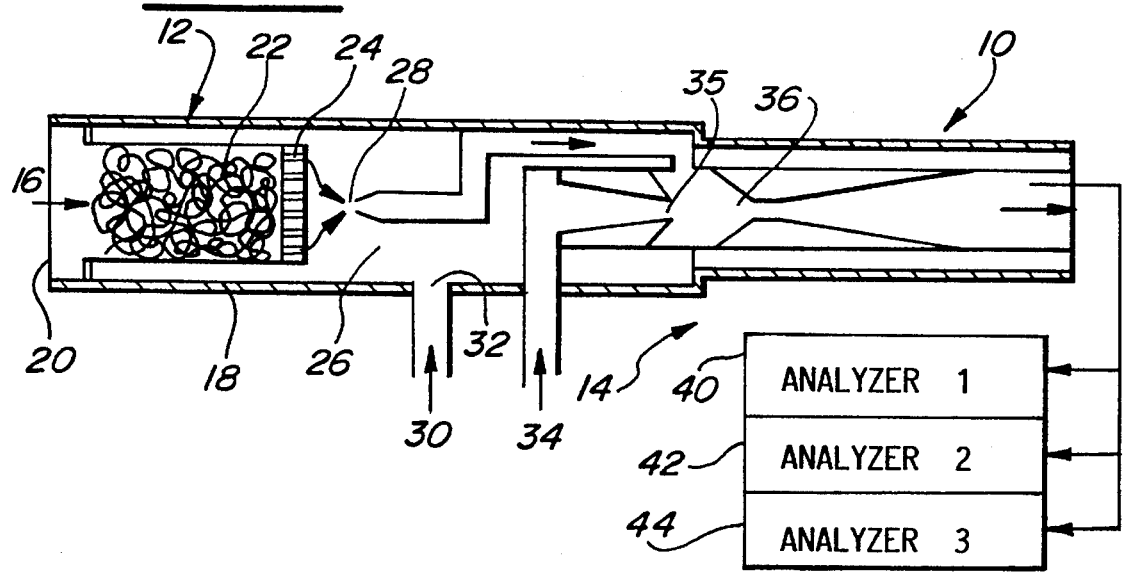
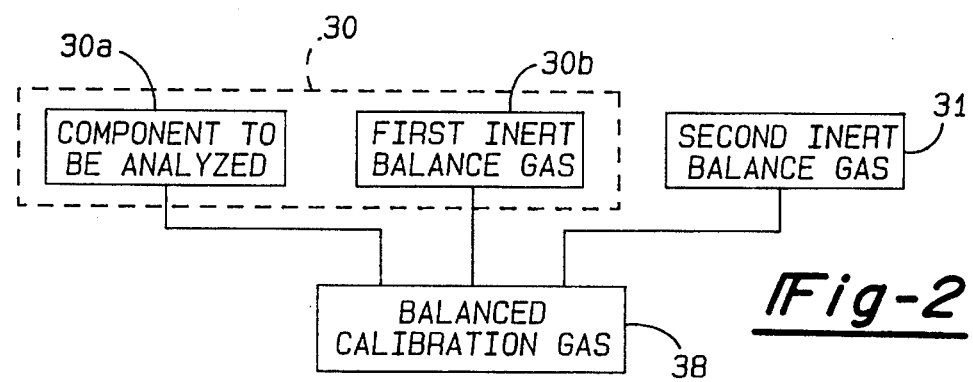
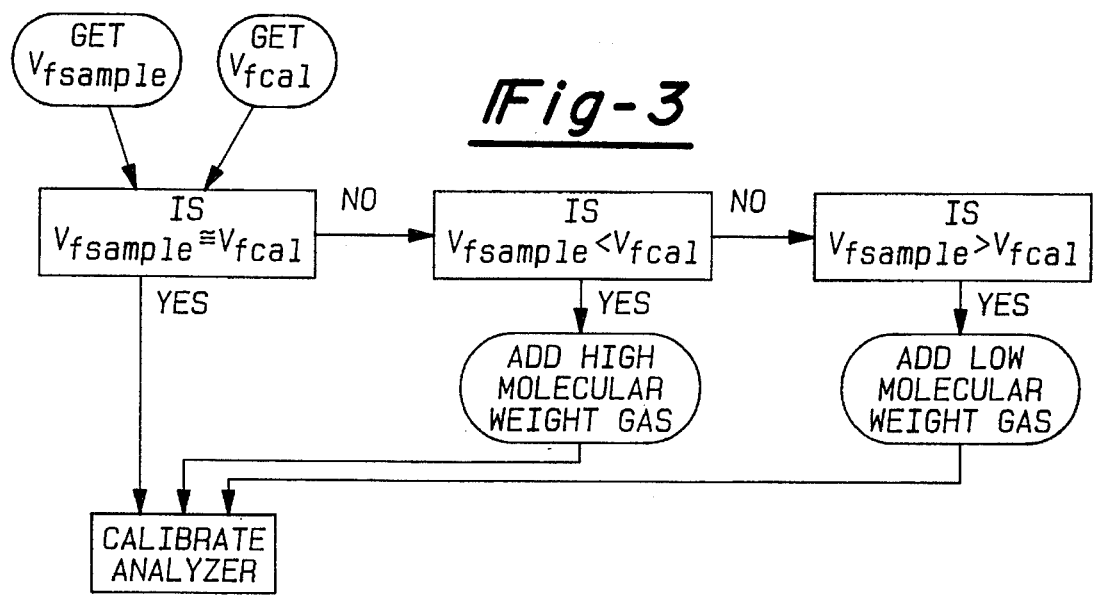

5,540,077

METHOD AND GAS MIXTURE FOR CALIBRATING AN ANALYZER

FIELD OF THE INVENTION

The present invention relates to a method of measuring the concentration of a component of a gas mixture, wherein the gas mixture flows through a critical orifice at sonic velocity prior to being diluted and then routed to an analyzer.

BACKGROUND OF THE INVENTION

Precisely measuring the concentration of a component of a sample gas mixture under flow conditions can be difficult, particularly when the sample is at high temperature and contains high concentrations of carbon dioxide and water vapor. A solution to this problem is to rapidly dilute the sample in air or inert gas prior to analysis.

Commercial measurement equipment typically includes a probe having a critical orifice within the housing of the probe to control the flow rate of sample into a diluent gas. A stream of a sample gas enters the probe and flows through the critical orifice at sonic velocity, that is, the velocity of sound in the gas mixture. The sample gas then flows into the diluent gas, and is diluted by a presumably known dilution ratio. The diluted sample gas is then routed to an analyzer which is in communication with the probe. The analyzer provides a reading concerning the concentration level of the component in the diluted sample gas.

To calibrate the analyzer prior to measurement of the component, a calibration gas having a known concentration of the component is used to verify concentration readings from the analyzer. During the calibration of the analyzer, the calibration gas also flows through the critical orifice of the probe at sonic velocity prior to dilution. Difficulties can be encountered with current measurement methods, particularly when the calibration gas includes a plurality of components (a multi-component calibration gas), wherein different components of the same calibration gas are used to calibrate different analyzers. These difficulties arise because the velocity of sound can vary significantly from one gas to another gas and therefore from one gas mixture to another gas mixture.

Although methods for measuring concentration levels of components of diluted sample gas are well known in the art, known prior art methods are deficient in providing consistent, reliable data for commercial use in some measuring applications. In known methods, the difference in the respective flow rates of the calibration gas and the sample gas through a critical orifice is simply assumed to be negligible, and therefore not accounted for in the analysis. Although the flow rate of a gas mixture is dependent on numerous factors, it is possible to approximately compensate for the difference in the flow rates by a mathematical factor in the calculation. In either instance, less than exact measurements are achieved. To address this problem in prior art methods, it has not been known until the present invention to physically affect the calibration gas so that the calibration gas has the same or similar flow rate through the critical orifice as the sample gas which is to be measured, or some other gas mixture to be used as part of the calibration process.

It is therefore a goal of the present invention to provide a method of controlling the flow rate of a gas mixture through a critical orifice to match the flow rate of a sample gas or some other selected gas or mixture of gases. It is a further goal of the invention to provide a calibration gas for use in calibrating an analyzer, wherein the calibration gas includes an additional gas or gases, the additional gas affecting the flow rate of the calibration gas through a critical orifice, but otherwise not affecting the analysis. It is a further goal to provide a calibration gas having a flow rate that is equal to the flow rate of the sample gas, or other selected gas, through the critical orifice at sonic velocity.

SUMMARY OF THE INVENTION

An inventive method for measuring the concentration of a component in a diluted gas mixture is disclosed in which a calibration gas mixture has an additional gas component added to adjust the flow rate at sonic velocity of the calibration gas through a critical orifice. The flow rate at sonic velocity of the calibration gas is adjusted to equal the flow rate at sonic velocity of a sample gas which is to be analyzed, or some other gas mixture to be used as part of the calibration process.

A method of measuring the concentration of a component in a sample gas comprises the steps of: determining the flow rate at sonic velocity of the sample gas through a critical orifice; determining the flow rate at sonic velocity of a calibration gas through the critical orifice; comparing the flow rate of the sample gas with the flow rate of the calibration gas; formulating the calibration gas with an additional gas to adjust the flow rate of the calibration gas to approximately equal the flow rate of the sample gas through the critical orifice at sonic velocity, thereby creating a balanced calibration gas; calibrating the analyzer with the balanced calibration gas, wherein a concentration reading of the component from the analyzer is compared with a known concentration of the component in the balanced calibration gas; and measuring the concentration of the component of the sample gas using the analyzer.

These and other features of the present invention can be best understood from the following specification and drawings, of which the following is a brief description.

BRIEF DESCRIPTION OF THE DRAWINGS

FIG. 1 is a schematic view of a gas measurement system.

FIG. 2 is a schematic view showing a balanced calibration gas formed by a blending together a quantity of the component to be analyzed and two balance gases of differing molecular weight; and FIG. 3 is a flow diagram of a method of calibrating an analyzer which measures the concentration of a component of a gas under flow conditions.

DETAILED DESCRIPTION OF THE PREFERRED EMBODIMENT

Referring now to FIG. 1, a gas measurement system 10 includes a probe 12 in communication with an analyzer assembly 14, which is typically located at a remote location with respect to probe 12. Gas measurement system 10 measures the concentration of a plurality of components of a sample gas 16 under flow conditions.

Probe 12 is generally cylindrical, and includes a housing 18 having a substantially circular cross-section. A stream of sample gas 16 enters probe 12 at an intake opening 20. A mesh screen covers intake opening 20. Sample gas 16 then passes through a filter 22 and through a ceramic plate 24 before filling a chamber 26. The critical orifice 28 having a generally circular cross-section is positioned within chamber 26. Sample gas 16 enters critical orifice 28 prior to being diluted and routed to analyzer assembly 14.

To calibrate analyzer assembly 14, a calibration gas 30 is selectively released through inlet 32. Inlet 32 is downstream of intake opening 20, and in proximity to critical orifice 28. Calibration gas 30 selectively enters chamber 26 to displace sample gas 16. The calibration gas fills chamber 26 and surrounds critical orifice 28. Calibration gas 30 includes known concentrations of one or more components and is used to verify readings from analyzer assembly 14. Calibration of analyzer assembly 14 is required to achieve accurate measurement readings concerning concentration of the components of sample gas 16.

Gas measurement system 10 is used in applications where it is desirable to dilute sample gas 16 before it is analyzed in analyzer assembly 14. Provision is made to similarly dilute calibration gas 30 prior to calibrating analyzer assembly 14. It is generally required that the dilution ratio remain constant both for sample gas 16 and calibration gas 30. To achieve this, either gas mixture is drawn through critical orifice 28 at a maximum flow rate 14, which, under normal conditions, is the velocity of sound in the gas mixture, also referred to as sonic or acoustic velocity. Next, the gas mixture is mixed with a diluent gas 34 which is supplied at a constant flow rate. The diluent gas is usually clean, dry air, although other gases such as nitrogen are sometimes used. The diluent gas flows through a nozzle 35 and into a venturi 36 downstream of critical orifice 28. The high velocity of the diluent gas leaving the nozzle 35 and entering the venturi 36 creates a vacuum that draws the gas mixture through critical orifice 28. The vacuum creates an absolute pressure downstream of the critical orifice, which is typically less than half the upstream absolute pressure.

Under the above conditions, the gas mixture flows through critical orifice 28 at sonic velocity. Under normal circumstances, this velocity cannot be exceeded, and therefore provides a maximum flow rate $V_f$ for the gas mixture. The flow rate $V_f$ therefore remains constant even if the vacuum is not constant. Assuming that the upstream pressure and the flow of diluent gas 34 are constant, the dilution ratio of the gas mixtures will remain constant. The diluted gas mixture then flows to analyzers assembly 14 for measurement of the concentration of each component of interest.

As is known to those skilled in the art, the velocity of sound varies significantly from gas to gas and therefore from mixture to gas mixture, so that the flow rates $V_f$ through a critical orifice vary. For example, the velocity of sound in nitrogen is approximately 1150 ft/sec, the velocity of sound in carbon dioxide 880 ft/sec, and the velocity of sound in helium about 3280 ft/sec. Therefore, depending on the concentration level of components of particular gas mixture, the flow rate $V_f$ at sonic velocity will vary from gas mixture to gas mixture. If the flow rate $V_f$ at sonic velocity of calibration gas 30 varies significantly from the flow rate $V_{fsample}$ sample gas 16, the variation must be accounted for, either by a mathematical adjustment in the calculation, or by the present invention.

Referring now to FIG. 2, the present invention involves adding an additional gas, such as a second inert balance gas 31, to the two gases otherwise comprising calibration gas 30 (specifically, a known concentration of the component to be analyzed 30a and a first inert balance gas 30b), thereby forming a balanced calibration gas 38. By substituting a quantity of the second inert balance gas 31 for a portion of the first inert balance gas 30b during formulation of the balanced calibration gas 38, the second inert balance gas 31 affects the flow rate $V_{fcal}$ of balanced calibration gas 38 through a critical orifice, but otherwise does not affect the analysis. Balanced calibration gas 38 has a flow rate $V_{fcal}$ at sonic velocity through critical orifice 28 that at least approximately equals that of sample gas 16, or some other selected gas or gas mixture.

Balanced calibration gas 38 contains one or more added compounds that will not interfere with the analysis of interest, but will otherwise change the flow rate $V_{fcal}$ at sonic velocity through critical orifice 28 to match that of sample gas 16. If the exact composition of sample gas 16 is unknown, estimations may be used. Generally, as will be discussed by example below, the added gas will have either a relatively high molecular weight, such as argon or $SF_6$, or a relatively low molecular weight, such as helium.

Referring now to the diagram of FIG. 3, the symbols in the diagram have the following meaning:

A: Determine the flow rate $V_{fsample}$ at sonic velocity of sample gas 16, or other gas to be matched, through critical orifice 28;

B: Determine the flow rate $V_{fcal}$ at sonic velocity of calibration gas 30 through critical orifice 28;

C: Determine whether the flow rate $V_{sample}$ at sonic velocity of sample gas 16 through critical orifice 28 approximately equals the flow rate $V_{fcal}$ at sonic velocity of calibration gas 30 through critical orifice 28;

D: Determine whether the flow rate $V_{fsample}$ at sonic velocity of sample gas 16 through critical orifice 28 is less than the flow rate $V_{fcal}$ at sonic velocity of calibration gas 30 through critical orifice 28;

E: Add an additional gas with a relatively high molecular weight to calibration gas 30 forming a balanced calibration gas, such that the flow rate $V_{fsample}$ at sonic velocity of sample gas 16 through critical orifice 28 approximately equals the flow rate at $V_{fcal}$ at sonic velocity of the balanced calibration gas through critical orifice 28;

F: Determine whether the flow rate $V_{fsample}$ at sonic velocity of sample gas 16 through critical orifice 28 is greater than the flow rate $V_{fcal}$ at sonic velocity of calibration gas 30 through critical orifice 28;

G: Add an inert gas with a relatively low molecular weight to calibration gas 30 forming a balanced calibration gas, such that the flow rate $V_{fsample}$ at sonic velocity of sample gas 16 through critical orifice 28 approximately equals the flow rate $V_{fcal}$ fat sonic velocity of the balanced calibration gas through critical orifice 28;

H: Calibrate an analyzer using the balanced calibration gas, verifying a reading concerning concentration of the component from the analyzer with a known concentration of the component in the balanced calibration gas.

The inventive method for measuring the concentration of a component in sample gas 16 as outlined above, comprises the steps of: determining the flow rate $V_{fsample}$ at sonic velocity of the sample gas through critical orifice 28, which is the maximum flow rate $V_f$ for sample gas 16; determining the flow rate $V_{fcal}$ at sonic velocity of calibration gas 30 through the critical orifice, which is the maximum flow rate $V_f$ for calibration gas 30; comparing the flow rate $V_{sample}$ at sonic velocity of the sample gas through the critical orifice with the flow rate $V_{fcal}$ at sonic velocity of the calibration gas through the critical orifice; adding an additional gas to the calibration gas to adjust the flow rate $V_{fcal}$ at sonic velocity of the calibration gas through a critical orifice, the flow rate $V_{fcal}$ at sonic velocity of the calibration gas being adjusted to approximately equal the flow rate $V_{fsample}$ at sonic velocity of the sample gas through the critical orifice, thereby creating a balanced calibration gas; calibrating analyzer assembly 14 with the balanced calibration gas, wherein an output from the analyzer concerning the concentration of a component is compared with a known concentration of the component in the balanced calibration gas; and measuring the concentration of the component in the sample gas using the analyzer. The determination of the flow rate $V_f$ at sonic velocity of a gas mixture through the critical orifice may be achieved by mathematical calculations, or by use of measurement equipment known to those skilled in the art.

Referring to FIG. 1, a gas mixture to be analyzed is routed to analyzer assembly 14. Analyzer assembly 14 may be any conventional gas analyzer system. As shown, the gas mixture may be routed to a first analyzer 40, a second analyzer 42, or a third analyzer 44. First analyzer 40 provides output information concerning the concentration levels of a first component in the gas mixture, such as nitric oxide; second analyzer 42 provides output information concerning the concentration levels of a second component in the gas mixture, such as sulfur dioxide; and third analyzer 44 provides output information concerning the concentration levels of a third component in the gas mixture, such as carbon dioxide.

A conventional analyzer assembly 14 responds to changes in gas mixture composition and produces an output such as voltage that can be correlated with the concentration of a component in the gas mixture. For example, nitric oxide analyzer 40 produces an output of 1.0 Volt (V) when a gas mixture of 1000 parts per million (ppm) of nitric oxide flows through it. This assumes that analyzer 40 is calibrated to produce an output of 0.0 V when a gas mixture having a zero concentration of nitric oxide flows through it.

The output of an analyzer in response to different component concentrations may be linear, close-to-linear or non-linear. If an analyzer response is linear, then the output is directly proportional to the concentration of the component in the gas mixture flowing through it. Calibration of an analyzer with respect to the linearity of output is known as a "linearity check." To perform a linearity check, analyzers 40, 42 and 44 are calibrated with a calibration gas that is also known as a "calibration gas standard." In some applications, a linearity check with a calibration gas is required periodically; for example four times each year.

Over a period of hours, the output of an analyzer in response to a particular component concentration will change due to drift in the electronics or changes in the environment. Therefore, before use and periodically thereafter, an analyzer must be checked against a zero gas (a gas having no concentration of the component) and a calibration gas (a gas having a known concentration of the component). The calibration gas is usually selected to have a concentration of the component at or near the maximum concentration to be measured on a particular range, and is used to set the span of the range. This type of calibration gas is typically referred to as a "span gas."

For example, to adjust the 0–1000 ppm range of a nitric oxide analyzer with a 0–1 Volt output would require a zero gas (with no nitric oxide) and a span gas containing nitric oxide at a concentration close to 1000 ppm. First, the zero gas is flowed through the analyzer and zero adjustment is set so that the output of the analyzer is 0.00 V. Next, the span gas is flowed through the analyzer and the span adjustment is set so the output is some standard value. This may be done every time the analyzer is used or less frequently such as weekly, monthly or even quarterly.

In many applications, sample gas 16 and calibrated gas 30 flow directly to analyzer assembly 14 and the desired component concentration is measured directly. In some cases, the condition of the sample gas requires some form of treatment to eliminate one or more analytical problems before the sample gas can flow to analyzer assembly 14. In these instances, the sample gas is diluted prior to analysis.

As an illustration, a conventional electric power plant using the combustion of oil or coal as a source of energy produces a "stack gas." Stack gas is shown as sample gas 16 in FIG. 1. A typical stack gas might have a composition of 12% carbon dioxide, 9% water, 500 ppm nitric oxide and 1000 ppm sulfur dioxide with the balance being nitrogen and a relatively small quantity of oxygen. The stack gas is typically diluted prior to analysis for several reasons. One purpose of dilution is to reduce the concentration of moisture in the stack gas. This prevents condensation of the moisture in the colder line carrying the stack gas to the analyzer and also eliminates changes in the concentration of the other components when the moisture is removed prior to entering the analyzers 40, 42, and 44. Another purpose of dilution is to reduce the concentrations of the components to be analyzed, usually carbon dioxide, nitric oxide and sulfur dioxide, so that these components do not interfere with the analyses of each other. For example, a high concentration of carbon dioxide in a gas mixture significantly affects the measurement of nitric oxide concentration in the same mixture.

Reference to Table 1 will be made to illustrate practice of the present invention. The ratios of specific heat and molecular weights of several gases of interest are provided with Table 1. Column 1 represents the relative concentration of a stack gas. The concentrations of nitric oxide and sulfur dioxide are not shown because they are generally so low that these components have a negligible effect on flow rates $V_f$ at sonic velocity. As will be explained, the other columns represent various calibration gases used to calibrate the analyzers 40, 42 and 44. Calibration involves periodic verification of the linearity of the readings from the analyzer, as well as setting the span in which readings for a particular component will be taken.

TABLE 1

| | $C_p/C_v = k$ | Molecular Weight M |
|---|---|---|
| Nitrogen | 1.404 | 28.016 |
| Argon | 1.668 | 39.944 |
| Helium | 1.630 | 4.003 |
| Carbon Dioxide | 1.304 | 44.010 |
| Water | 1.330 | 18.016 |

| Column: | 1 | 2 | 3 | 4 | 5 | 6 | 7 | 8 | 9 | 10 | 11 |
|---|---|---|---|---|---|---|---|---|---|---|---|
| Nitrogen | 79.0% | 99.9% | 82.0% | 89.0% | 95.0% | 78.0% | 76.3% | 87.2% | 87.0% | 92.3% | 77.0% |

TABLE 1-continued

| | | | | | | | | | | | |
|---|---|---|---|---|---|---|---|---|---|---|---|
| Argon | | | | | | 22.0% | | | 8.0% | | 16.4% |
| Helium | | | | | | | 5.7% | 1.8% | | | 1.6% |
| Carbon Dioxide | 12.0% | | 18.0% | 11.0% | 5.0% | | 18.0% | 11.0% | 5.0% | 7.7% | 5.0% |
| Water | 9.0% | | | | | | | | | | |
| Mixture-k | 1.385 | 1.404 | 1.386 | 1.393 | 1.399 | 1.462 | 1.399 | 1.397 | 1.420 | 1.396 | 1.446 |
| Mixture-M | 29.035 | 28.016 | 30.895 | 29.775 | 28.816 | 30.640 | 29.298 | 29.271 | 29.770 | 29.248 | 30.328 |
| k/M | 0.048 | 0.050 | 0.045 | 0.047 | 0.049 | 0.048 | 0.048 | 0.048 | 0.048 | 0.048 | 0.048 |
| SORT (k/M) | 0.218 | 0.224 | 0.212 | 0.216 | 0.220 | 0.218 | 0.219 | 0.218 | 0.218 | 0.218 | 0.218 |
| Mix Vel | 1.000 | 1.025 | 0.970 | 0.990 | 1.009 | 1.000 | 1.000 | 1.000 | 1.000 | 1.000 | 1.000 |

In order to practice the method of the present invention, the sonic velocity in sample gas 16 and calibration gas 30 must be determined. The velocity of sound (sonic or acoustic velocity), $u_c$, in a gas can be calculated from the following equation:

$$u_c = \sqrt{(g_c\, R\, T\, k/M)},$$

where
$g_c$=dimensional constant
R=gas constant
T=absolute temperature
k=ratio of specific heat at constant pressure to that at constant volume (Cp/Cv)
M=molecular weight.

Based on this formula, at constant temperature, the sonic velocity in a gas is proportional to the value of $\sqrt{(k/M)}$. Relevant data used in determining the flow rate at sonic velocity for the gas mixtures are also shown on Table 1.

A method of calibrating an analyzer involves the use of a single component calibration gas. A separate set of single component calibration gases are provided for each analyzer. Typically, three calibration gases are provided for each analyzer, each having a varying concentration of the component to be analyzed. For example, analyzer 40 is calibrated with three calibration gases, each having a varying concentration of nitric oxide; analyzer 42 is calibrated with three separate calibration gases, each having a varying concentration of sulfur dioxide; and analyzer 44 is calibrated with three calibration gases, each having a varying concentration of carbon dioxide. To calibrate three analyzers, nine calibration gas standards would be used.

For the nitric oxide and sulfur dioxide calibration gas standards, greater than 99% of the gas is nitrogen so that the sonic velocities are generally the same and approximately equal to nitrogen. The sonic velocity and ratio to stack gas for the single component calibration gas standards for nitric oxide and sulfur dioxide are represented in column 2 of Table 1. As previously discussed, the presence of nitric oxide and sulfur dioxide have a negligible effect on sonic flow. The dilution of each of the three calibration gas standard for each component will be the same. However, the sonic velocity of a single component calibration gas standard for either nitric oxide or sulfur dioxide is 2.5% higher than that of the stack gas, comparing column 1 with column 2 of Table 1. Therefore, the dilution of the stack gas will be higher due to the reduced sonic flow rate, and the measured values of nitric oxide and sulfur dioxide concentration in the stack gas will produce an analyzer output 2.5% lower than the true values. This discrepancy has provided acceptable results when single component calibration gases are used for nitric oxide and sulfur dioxide analyzers.

For the carbon dioxide calibration gas standards, however, each calibration gas standard for carbon dioxide has a different sonic velocity, and therefore, a different flow rate. Columns 3, 4, and 5 of Table 1 show the relative sonic velocities for a typical set of single component calibration gas standards for carbon dioxide.

Referring more specifically to columns 4 and 5, the sonic velocities for the 11% and 5% single component calibration gas standards are higher so that their dilution's will be lower. Therefore, if the analyzer is spanned with the 18% calibration gas, the measured concentration of the 11% calibration gas (used for the linearity check) will be 2.1% lower (0.212/0.216) than true value. Similarly, the measured value of the 5% calibration gas (also used for linearity testing) will be 4.0% lower (0.212/0.220) than true value. Depending on the linearity tolerance for the calibration of the analyzer, this may or may not be acceptable.

The above method using single component calibration gas provides less than accurate calibration of the analyzers. As will be discussed, the present invention may be used to overcome these shortcomings, and provide more accurate data.

A more recent method used to calibrate the analyzers compounds the shortcomings of the single component calibration gas method. To reduce the number of calibration gases that must be used for calibrating the analyzer, the recent trend is to use a calibration gas that contains all three components in a single mixture, referred to as "a multi-component calibration gas." The multi-component calibration gas has a given concentration of each of the three components being analyzed, namely carbon dioxide, nitric oxide and sulfur dioxide. Successive multi-component calibration gases progressively vary the concentration of each component. Therefore, the number of calibration gases required to calibrate three analyzers is reduced from nine to three.

One problem with this more recent method is that each of the three multi-component calibration gas standards has a different sonic velocity, and therefore has a different flow rate $V_f$. This is due to the presence of carbon dioxide at relatively high concentration in each of the multi-component calibration gas standards. Accurate calibration of the nitric oxide analyzer 40 and the sulfur dioxide analyzer 42 is therefore difficult with the multi-component calibration gas.

The multi-component calibration gas standards are represented in columns 3, 4 and 5 of Table 1. Because the concentrations of nitric oxide and sulfur dioxide have a negligible effect on sonic velocity in the gas mixture, and therefore a negligible effect on the flow rate $V_f$ at sonic velocity, these components are not shown. As seen in column 3, a multi-component calibration gas having 18% carbon dioxide has a sonic velocity ratio with the stack gas of 0.970. As seen in column 4, a multi-component calibration gas having 11% carbon dioxide has a sonic velocity ratio with the stack gas of 0.990. As seen in column 5, a multi-component calibration gas having 5% carbon dioxide has a sonic velocity ratio with the stack gas of 1.009.

Whether the single component calibration gas or the multi-component calibration gas are used to calibrate the analyzers, the differences in flow rate at sonic velocity must be accounted for in order to accurately calibrate the analyzers. To achieve this, the method of the present invention modifies the flow rate $V_{fcal}$ at sonic velocity of the calibration gas by adding an additional gas during its formulation that will not affect the analysis of interest, but will affect the flow rate $V_{fcal}$ of the resulting balanced calibration gas.

To practice the invention, a second inert balance gas 31 is blended with the component to be analyzed 30a and the first inert balance gas 30b to form the balanced calibration gas 38. Balanced calibration gas 38 has a flow rate $V_{fcal}$ at sonic velocity through critical orifice 28 that approximately equals that of sample gas 16. Generally, the first inert balance gas 30b is nitrogen, and the second inert balance gas 31 will have either a relatively low molecular weight, such as helium, or a relatively high molecular weight, such as argon or $SF_6$.

For example, the flow rate $V_{fcal}$ of a single component calibration gas with 900 ppm nitric oxide, which is 2.5% higher than stack gas, can be corrected to match that of sample gas 16 by formulating it with 78% nitrogen and 22% argon as shown in column 6 of Table 1. The flow rate $V_{fcal}$ of a calibration gas with 18% carbon dioxide, which is 3.0% lower than stack gas, can be corrected to match that of sample gas 16 by formulating it with 76.3% nitrogen and 5.7% helium, as shown in column 7. A calibration gas with 11% carbon dioxide can be corrected by the addition of 1.8% helium as shown in column 8 of Table 1. A calibration gas with 5% carbon dioxide can be corrected formulating it with 87% nitrogen and 8% argon as shown in column 9 of Table 1. Column 10 of Table 1 shows that a gas with 7.7% carbon dioxide would not require correction to match the sonic velocity of this particular stack gas.

By way of further example, it may be convenient for purposes of producing balanced calibration gases 38 to maintain a constant helium to nitrogen ratio. Therefore, to correct the mixtures with 11% and 5% carbon dioxide, a blend of inert balance gases 2 parts helium to 98 parts nitrogen could be used for producing both the 11% $CO_2$ and 5% $CO_2$ balanced calibration gases formulated as shown in columns 8 and 11 of Table 1, respectively, if 16.4% argon is also added when formulating to the 5% carbon dioxide mixture, as shown in column 11.

In some instances it may be desirable to match the sonic velocity of one or more calibration gases to a mixture other than the sample gas 16. This may be the case if it is more important to an operator to meet a linearity specification for analyses, rather than an absolute accuracy specification. For example, if a multi-component gas standard with 18% carbon dioxide is to be used to span the analyzers, the sonic velocities of multi-component standards with 11% carbon dioxide and 5% carbon dioxide could be balanced to have the same sonic velocities as the 18% standard by the addition of about 20% and 40% argon, respectively. The concentrations of each component after dilution in the probe would then be linear as required. Alternatively, the sonic velocities of multi-component standards could be matched to single component standards, which are essentially nitrogen, by the addition of appropriate concentrations of helium.

The embodiments disclosed herein have been discussed for the purpose of familiarizing the reader with the novel aspects of the invention. Although preferred embodiments of the invention have been shown and described, many changes, modifications and substitutions may be made by one having ordinary skill in the art without necessarily departing from the spirit and scope of the invention as described in the following claims.

What is claimed is:

1. A method of calibrating an analyzer which generates a first output responsive to the concentration of a first component of a first gas mixture, wherein the first gas mixture is drawn through a critical orifice at the sonic velocity of the first gas mixture and thereafter diluted with a substantially constant flow of a diluent gas prior to being supplied to the analyzer, the method comprising the steps of:

providing a second gas mixture, said second gas mixture including the first component in a first known concentration and at least two inert balance gases, the relative concentrations of said balance gases in said second gas mixture being such that the sonic velocity of said second gas mixture is approximately equal to the sonic velocity of the first gas mixture;

drawing said second gas mixture through the critical orifice at sonic velocity;

diluting said drawn second gas mixture with the substantially constant flow of the diluent gas;

supplying said diluted drawn second gas mixture to the analyzer; and comparing a second output from the analyzer responsive to the concentration of the first component in the diluted drawn second gas mixture with the first known concentration of the first component in said second gas mixture.

2. The method of claim 1, including the steps of:

providing a third gas mixture, said third gas mixture including the first component in a second known concentration and at least two inert balance gases, the relative concentrations of said balance gases in said third gas mixture being such that the sonic velocity of said third gas mixture is approximately equal to the sonic velocity of the first gas mixture, and wherein the second known concentration of the first component in said third gas mixture is different from the first known concentration of the first component in said second gas mixture;

drawing said third gas mixture through the critical orifice at sonic velocity;

diluting said drawn third gas mixture with the substantially constant flow of the diluent gas;

supplying said diluted drawn third gas mixture to the analyzer; and comparing a third output from the analyzer responsive to the concentration of the first component in the diluted drawn third gas mixture with the second known concentration of the first component in said third gas mixture.

3. The method of claim 1, wherein one of said at least two balance gases of said second gas mixture has a relatively high molecular weight with respect to the first gas mixture.

4. The method of claim 1, wherein one of said at least two balance gases of said second mixture has a relatively low molecular weight with respect to the first gas mixture.

5. The method of claim 1, wherein the first gas mixture is a sample gas having an unknown concentration of the first component.

6. The method of claim 1, wherein the first gas mixture includes the first component in a third known concentration.

7. A calibrating gas mixture for calibrating an analyzer which generates a first output responsive to the concentration of a first component of a first gas mixture after the first gas mixture is drawn at maximum flow rate through a critical orifice and subsequently diluted with a substantially constant stream of a diluent gas, said calibrating gas mixture comprising:

the first component in a first known concentration; and at least two inert balance gases, each of said at least two balance gases having different molecular weights, wherein the concentration of each of said at least two balance gases in said calibrating gas mixture are such that the velocity at which sound travels through said calibrating gas mixture is approximately equal to the velocity at which sound travels through the first gas mixture.

8. The calibrating gas mixture of claim 7, wherein one of said balance gases is nitrogen.

9. The calibrating gas mixture of claim 7, wherein the first component is one of the group consisting of carbon dioxide, nitric oxide and sulfur dioxide; and wherein another of said balance gases is helium.

10. The calibrating gas mixture of claim 9, wherein said calibrating gas mixture further comprises a second component in a second known concentration, said second component being another of the group consisting of carbon dioxide, nitric oxide and sulfur dioxide.

11. The calibrating gas mixture of claim 7, wherein the first component is one of the group consisting of carbon dioxide, nitric oxide and sulfur dioxide; and wherein another of said balance gases is argon.

12. The calibrating gas mixture of claim 11, wherein said calibrating gas mixture further comprises a second component in a second known concentration, said second component being another of the group consisting of carbon dioxide, nitric oxide and sulfur dioxide.

13. The calibrating gas mixture of claim 7, wherein the first gas mixture is a sample gas comprising the first component in an unknown concentration.

14. The calibrating gas mixture of claim 7, wherein the first gas mixture is a second calibrating gas mixture having a second known concentration of the first component.

15. A method of manufacturing a calibrating gas mixture for use in calibrating an analyzer, wherein the analyzer measures the concentration of a first component of a first gas mixture after the first gas mixture is drawn at a maximum flow rate through a critical orifice and thereafter diluted with a substantially constant flow of a diluent gas, the method comprising the step of blending together a quantity of the first component and a quantity of each of at least two inert balance gases, each balance gas having a different molecular weight, the relative quantities of the first component and said balance gases being such that the velocity at which sound travels through the calibrating gas mixture is approximately equal to the velocity at which sound travels through the first gas mixture.

16. The method of claim 15, wherein one of the balance gases is nitrogen and another of the balance gases is helium.

17. The method of claim 15, wherein one of the balance gases is nitrogen and another of the balance gases is argon.

18. The method of claim 15, wherein the first component is one of the group consisting of carbon dioxide, nitric oxide and sulfur dioxide; and one of said balance gases is helium.

19. The method of claim 15, wherein the first component is one of the group consisting of carbon dioxide, nitric oxide and sulfur dioxide; and one of said balance gases is argon.

* * * * *